United States Patent [19]

Mackay et al.

[11] 4,291,045
[45] Sep. 22, 1981

[54] METHOD OF REDUCING DENTAL CARIES

[75] Inventors: Donald A. M. Mackay, Pleasantville; Frank Witzel, Spring Valley, both of N.Y.; Harald A. B. Linke, Highland Park, N.J.

[73] Assignee: Life Savers, Inc., New York, N.Y.

[21] Appl. No.: 152,886

[22] Filed: May 23, 1980

Related U.S. Application Data

[63] Continuation of Ser. No. 683,108, May 4, 1976, abandoned.

[51] Int. Cl.$^3$ .................. A61K 31/425; A61K 9/68; A61K 7/16; A61K 7/22
[52] U.S. Cl. .................. 424/270; 424/48; 424/49; 424/54; 426/3; 426/648; 426/660
[58] Field of Search .................. 424/270

[56] References Cited

U.S. PATENT DOCUMENTS

| | | | |
|---|---|---|---|
| 280,115 | 6/1883 | Aurin | 426/3 |
| 2,725,326 | 11/1955 | Shibe et al. | 424/329 |
| 3,065,123 | 11/1962 | Hinton et al. | 162/161 |
| 3,983,214 | 9/1976 | Misato et al. | 424/180 |
| 4,045,581 | 8/1977 | Mackay et al. | 426/3 |
| 4,064,274 | 12/1977 | Mackay et al. | 426/3 |
| 4,065,579 | 12/1977 | Mackay et al. | 426/3 |
| 4,085,227 | 4/1978 | Mackay et al. | 426/3 |
| 4,087,557 | 5/1978 | Bakal et al. | 426/3 |
| 4,238,475 | 12/1980 | Witzel et al. | 424/48 |

FOREIGN PATENT DOCUMENTS

| | | |
|---|---|---|
| 49-109535 | 10/1974 | Japan . |
| 52-105216 | 9/1977 | Japan . |
| 52-110830 | 9/1977 | Japan . |
| 53-66424 | 6/1978 | Japan . |
| 1066795 | 4/1967 | United Kingdom . |
| 1330531 | 9/1973 | United Kingdom . |

OTHER PUBLICATIONS

Linke, H. et al., Z. Naturforsch, C. Biosci. 1976, 31C (5–6): 245–251 Physiological Effects of Sucrose Substitutes and Artificial Sweeteners on Growth Pattern and Acid Production of Glucose-Grown *Streptococcus mutans* Strains in Vitro.

Linke, H., Z. Naturforsch, C. Biosci. 1977, 32C (9–10): 839–843 Growth Inhibition of Glucose-Grown Cariogenic and Other Streptococci by Saccharin in Vitro.

*Primary Examiner*—Shep K. Rose
*Attorney, Agent, or Firm*—Lawrence S. Levinson; Burton Rodney

[57] ABSTRACT

A method for treating teeth to reduce caries is provided wherein the teeth are contacted with a saccharin material, optionally in the presence of a sugar, for example, as contained in a chewing gum composition, the saccharin material being present in an amount sufficient to inhibit growth of *Streptococcus mutans* in the oral cavity or on the teeth.

2 Claims, 1 Drawing Figure

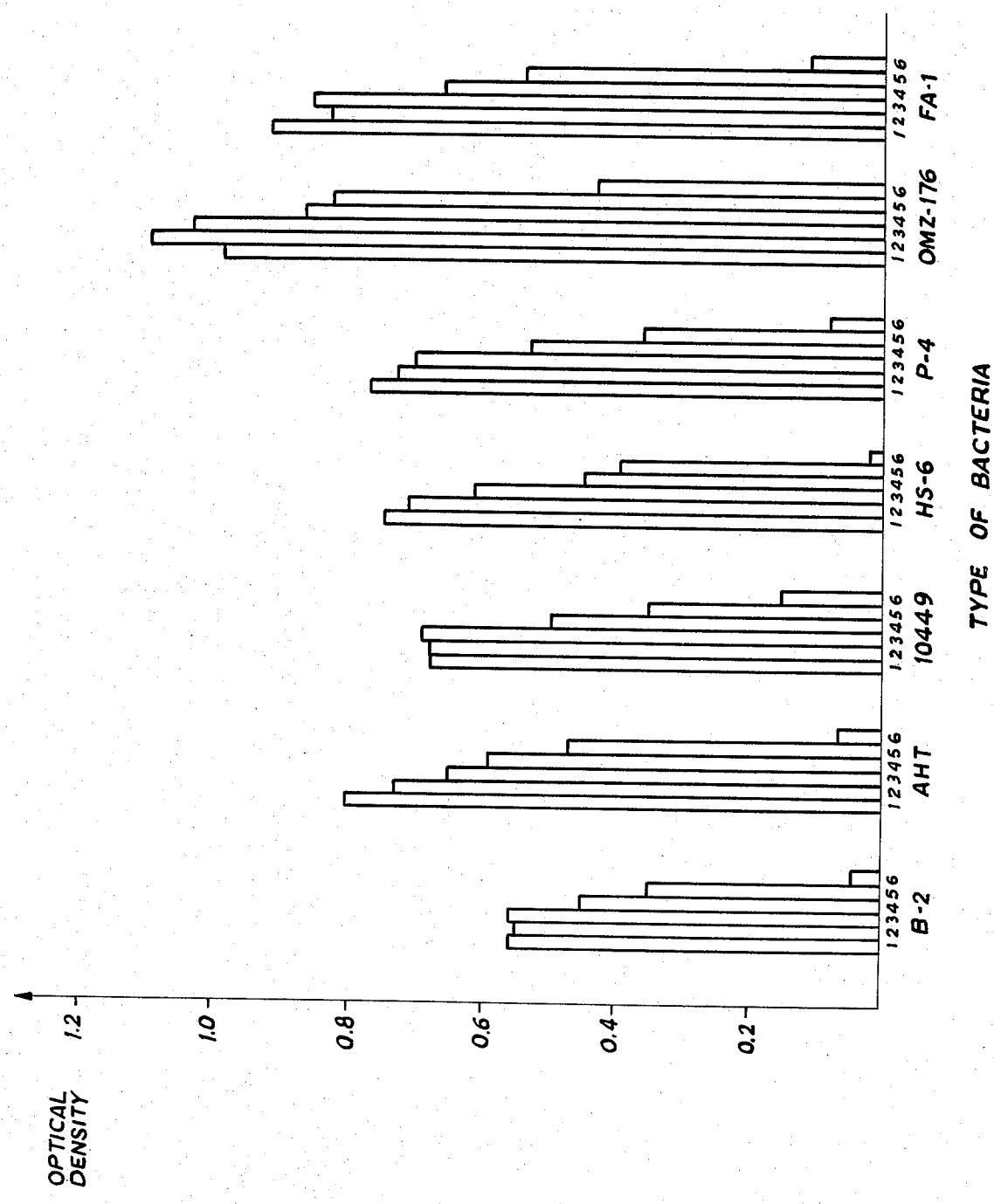

METHOD OF REDUCING DENTAL CARIES

This is a continuation of application Ser. No. 683,108, filed May 4, 1976, now abandoned.

The present invention relates to a method for preventing or reducing dental caries wherein a saccharin material is employed to inhibit growth of *Streptococcus mutans* in the oral cavity.

Foods containing natural sugars such as sucrose and glucose have long been recognized as a major contributing cause of dental caries. The sugars are an easily utilizable source of nutrition for bacteria, such as *Streptococcus mutans* found in the oral cavity, which bacteria is responsible for the formation of plaques on the surface of the teeth, due to dextran and levan production from sucrose. The levan-containing plaques absorb further amounts of sugar and thus provide a ready source of nutrition for bacteria adjacent the surface of the teeth even while the host is asleep. The bacteria acting on the residue sugar or levan in the plaques results in fermentation and rapid transformation of the sugar or levan into acids which, upon reaching the "critical" pH of 5.50, dissolve the minerals of the teeth.

In an effort to reduce tooth decay, artificial sweeteners, such as saccharin salts and cyclamate salts have been employed as sugar substitutes in many foods. However such foods have not been entirely accepted by the consuming public, and especially by children, because of the metallic or bitter after-taste characteristic of the usual forms of artificial sweeteners. The use of non-fermentable carbohydrates such as polyhydric alcohols like sorbitol, mannitol and xylitol have been employed in place of sugars in chewing gums and confections. Moreover, these non-sugar bulking agents have been found to be physically inferior in taste, stability, and manufacturing ease to the sugar normally used.

It has now been found that the use of saccharin material in foods, confections, chewing gum, beverages and the like as a natural sugar substitute or in combination with natural sugars provides an especially effective tool in the fight against dental caries and prevention and inhibition of tooth decay. Surprisingly and unexpectedly, the saccharin material has been found to inhibit growth of *Streptococcus mutans* strains of bacteria, a prime contributor to formation of dental plaque and tooth decay.

Thus, in accordance with the present invention a method is provided for treating teeth to inhibit or prevent caries, wherein the teeth are contacted with a saccharin material in an amount sufficient to inhibit growth of *Streptococcus mutans* present in the oral cavity or on the teeth.

The terms "saccharin", "saccharin compound" and "saccharin material" as employed herein include the readily available soluble saccharin salts, such as calcium saccharin, sodium saccharin and ammonium saccharin, or the relatively insoluble forms of saccharin, such as the free acid form of saccharin.

In carrying out the method of the invention, the saccharin compound will usually be employed in conjunction with a non-toxic edible carrier to form a food, confection, chewing gum, dental tablet, cream or paste, beverage and the like. Regardless of the form of the composition or carrier, the total amount of saccharin compound present in the composition will preferably be beyond the normal organoleptic threshold of sweetness and bitterness. Thus, the saccharin compound may be employed in amounts ranging from about 0.008 to about 1% or more by weight, and preferably from about 0.06 to about 0.4% by weight of the total composition.

It appears that the effectiveness of the saccharin compound in inhibiting plaque formation increases with increasing saccharin-teeth exposure or contact time. Thus, the presence of relatively small amounts of saccharin compound solubilized in the saliva over extended periods of time (for example, 1 to 300 mg of saccharin compound over a period of 5, 10, 20, 30 minutes or more) is, for the purposes of the present invention, more desirable than the presence of large or peak amounts of saccharin compound solubilized in the saliva for relatively short periods of time (for example, 1 to 300 mg of saccharin compound over a period of 1 to 4 minutes). Thus, the saccharin compound will preferably be provided in a form or composition so that it may be controlledly or slowly released and solubilized in relatively small quantities in the saliva over extended periods of time; moreover, although large amounts of saccharin compound may be initially present, at any given time, amounts of saccharin material which are organoleptically acceptable (that is, below the bitterness threshold and below the undesirably oversweet threshold) will be solubilized in the saliva and available for tasting.

The saccharin compounds, especially the soluble saccharin salts, will thus preferably be provided in a form to ensure relatively slow release or solubilization in the saliva. Thus, for example, the saccharin compound may be coated with, integrated with or encapsulated with non-toxic water-insoluble polymeric substances such as polyvinyl esters, disclosed in U.S. Pat. Nos. 3,826,847 and 3,795,744, organic acids as disclosed in U.S. Pat. No. 3,761,288, or other known edible materials as, for example, any of the fusing agents disclosed in U.S. Pat. No. 3,928,633, as well as hydrophilic colloids such as ethyl cellulose, paraffin wax or sodium alginate. The saccharin compound so-modified and employed in conjunction with conventional carriers as described above, will be slowly solubilized in the saliva over extended periods of time.

Where the saccharin compound is employed in a chewing gum composition, in order to achieve slow release, the saccharin compound will be employed in particulate form having an average particle size of below about 150 microns (0.150 mm or about 100 mesh), and will be incorporated into the gum base portion of the chewing gum. The particulate saccharin compound will be substantially retained in the gum base, and during chewing undergoes slow and controlled release into the saliva. An average stick or tablet of gum will preferably contain from about 2 to about 25 mg of saccharin compound.

It is well known that fine pulverization of crystals or poorly soluble materials or slowly dissolving materials of even good solubility increases surface area thereof, which, in turn, increases solubility rate. However, it has been surprisingly and unexpectedly found that finely divided saccharin compounds, such as finely powdered free saccharin acid, or the soluble saccharin salts, when incorporated into chewing gum base do just the opposite; the extraction rate of such saccharin compounds from the gum base during chewing is reduced with decreasing particle size. The result is that relatively small concentrations of solubilized saccharin compound (albeit concentrations above the organoleptic sweetness threshold thereof) will be present in the saliva over prolonged periods of time. The reason for this effect would seem to be that at the finer particle sizes, the saccharin compound is more completely protected from contact with saliva by the gum base. This results in controlled release of saccharin compound from the gum base.

The slowly or controlledly released saccharin containing chewing compositions employed in the method of the invention may be prepared by admixing melted gum base with a plasticizer, such as a syrupy substance, for example corn syrup, or a modified starch syrup or sorbitol syrups, at a temperature ranging from about 180° to about 210° F., to form a base-syrup mix, optionally adding flavor oil to the mix, during the first five minutes of mixing while the mix is folding well admixing the base-syrup mix with particulate saccharin compound, to form a continuous gum mass having the particles of saccharin compound intimately dispersed therein, and thereafter, optionally admixing the above mix with one or more easily extractable water-soluble sweeteners, such as natural sugar, soluble saccharin salts, water-soluble food acid and/or flavors. The resulting mix is then formed into sticks or tablets of chewing gum employing conventional techniques.

In carrying out the above method, it is preferred that the saccharin compound be poorly water-soluble, such as the free saccharin acid, so that is will not dissolve in the plasticizer (which normally will be an aqueous plasticizer such as corn syrup) before it is transferred to the gum base. However, where non-aqueous plasticizers are employed, the saccharin material may be of the water-soluble type, such as the saccharin salts.

Where it is desired to employ the soluble saccharin salts in a chewing gum containing an aqueous plasticizer, the soluble saccharin salts will be added to the gum base ingredients before the aqueous plasticizer is added thereto. In this manner, the soluble saccharin salts will be transferred to the gum base and will not be first dissolved in the plasticizer.

In addition, particles of water-soluble saccharin salt may be treated to make them less soluble or even insoluble such as by conventional coating or encapsulating techniques as described above, for example, as described in U.S. Pat. Nos. 3,795,744 and 3,826,847. The so-treated particles may be added to the gum base either before or after plasticizer (aqueous or non-aqueous) is added thereto. Regardless of the solubility of the saccharin compound, it is preferred that the particles of saccharin compound have an average particle size of less than 150 microns to ensure slow controlled release into the saliva.

By following the above procedures, the finely divided saccharin compound will be incorporated and retained in the gum base and will undergo controlled release in the mouth for periods of up to 30 minutes or more to provide concentrations of the saccharin compound below the bitter threshold thereof, but in sufficient amounts to inhibit growth of *Streptococcus mutans* and to provide pleasant sweet taste.

The chewing gum will include a relatively water-insoluble, water-impenetrable gum base in an amount ranging from about 8 to about 50%, and preferably from about 15 to 30% by weight of the chewing gum composition.

In general, the gum base is prepared by heating and blending various ingredients, such as, natural gums, synthetic resins, waxes, plasticizers, etc., in a manner well known in the art. Typical examples of the ingredients found in a chewing gum base are masticatory substances of vegetable origin, such as chicle, crown gum, nispero, rosidinha, jelutong, pendare, periollo, niger gutta, tunu, etc., masticatory substances of synthetic orign, such as butadiene-styrene polymer, isobutylene-isoprene copolymer, petroleum wax, polyethylene, polyisobutylene, polyvinylacetate, etc., plasticizers, such as lanolin, stearic acid, sodium stearate, potassium stearate, etc., antioxidants, such as, butylated hydroxyanisole, butylated hydroxytoluene, and propyl gallate.

The water-insoluble gum base may consist of any of the various bases disclosed for example in U.S. Pat. Nos. 3,052,552 and 2,197,719. Typical ingredients included in gum base compositions are the following:

|  | Parts by Weight |
| --- | --- |
| Base I | |
| Ester gum | 88 |
| Rubber latex solids | 10 |
| Lecithin | 2 |
| Base II | |
| Chicle | 30 |
| Jelutong | 60 |
| Gutta soh | 8.5 |
| Lecithin | 2 |
| Base III | |
| Partially oxidized chicle | 98 |
| Lecithin | 2 |
| Base IV | |
| Jelutong (dry) | 80 |
| Gutta siak | 18 |
| Lecithin | 2 |

The chewing gum may also include flavoring, such as sour or fruit flavoring or non-acid or mint flavoring in an amount ranging from about 0.3 to about 2.0% by weight, and preferably from about 0.5 to about 1.2% by weight of the final gum product. The flavoring may comprise synthetic flavors and oils derived from plants, leaves, flowers, fruit, etc. Representative flavor oils of this type include acids such as adipic, succinic and fumaric acid, citrus oils such as lemon oil, orange oil, lime oil, grapefruit oil, fruit essences such as apple essence, pear essence, peach essence, strawberry essence, apricot essence, raspberry essence, cherry essence, plum essence, pineapple essence, as well as the following essential oils: peppermint oil, spearmint oil, mixtures of peppermint oil and spearmint oil, clove oil, bay oil, anise oil, eucalyptus oil, thyme oil, cedar leaf oil, cinnamon oil, oil of nutmeg, oil of sage, oil of bitter almonds, cassia oil, and methylsalicylate (oil of wintergreen). Various synthetic flavors, such as mixed fruit, may also be incorporated in the chewing gum with or without conventional preservatives.

Where liquid flavors are employed, they may be added to the gum base-syrup mix as in the case of the particulate saccharin compound, that is, during the first five minutes of mixing, before a continuous mass of the gum base has been formed. Furthermore, after sugar (where present) has been mixed in with the gum base, any of the above flavors, in the form of spray dried flavor with or without citric acid may be added.

In order to provide an initial taste or sensation of sourness, the chewing gum may also preferably contain an easily extractable food acid, for example, a water-soluble food acid, such as citric acid, tartaric acid or malic acid, in an amount ranging from about 0.3 to about 2.0% by weight, and preferably from about 0.5 to about 1.2% by weight of the final gum product. The chewing gum may also include, in addition to or in lieu of the easily extractable food acid, a poorly water-soluble food acid such as fumaric acid, succinic acid, or adipic acid in amounts ranging from about 0.5 to about 3.5% by weight of the chewing gum. The poorly water-soluble food acid will have a particle size of less than about 150 microns and will be retained in the gum base in a manner similar to the saccharin compound. Where relatively large amounts of saccharin compound are present in the chewing gum (that is approaching the undesirably oversweet threshold) the chewing gum may contain the food acid (preferably the poorly water-soluble food acid alone or in combination with the water-soluble food acid) so that excessive sweetness may be counteracted with the food acid to provide a pleasant balanced sweet-sour taste.

Regardless of the form of the saccharin-containing composition, whether it be a chewing gum or otherwise, as will be seen herein, the saccharin compound may be employed in combination with a natural sugar such as sucrose or glucose. Inasmuch as the sugar, by itself, contributes to formation of dental plaque, the saccharin compound may be said to function as an anti-plaque antidote to sugar and inhibit plaque formation. The natural sugar may be present in an amount ranging from about 90 to about 0.05%, preferably from about 90 to about 40%, and more preferably from about 85 to about 70% by weight of the final product.

The term "natural sugar" includes sugar alcohols, such as xylitol, sorbitol or mannitol as well as one or more sugars or sugar containing material, for example, monosaccharides, disaccharides and polysaccharides, some examples of which follow:

A. Monosaccharides of 5 to 6 carbon atoms—arabinose, xylose, ribose, glucose, mannose, galactose, fructose, dextrose, or sorbose or mixtures of two or more of the foregoing monosaccharides.

B. Disaccharides—sucrose such as cane or beet sugar, lactose, maltose or cellobiose; and C. Polysaccharides—partially hydrolyzed starch, dextrin or corn syrup solids.

Generally, in forming the saccharin-sugar containing composition, the saccharin compound will be employed in a weight ratio to the natural sugar (water-soluble) sweetener within the range of from about 0.00022:1 to about 20:1 and preferably within the range of from about 0.0011:1 to about 0.01:1.

Of course, the saccharin compound need not be employed with the sugar; sugar consumed separately from the saccharin compound or even sugar produced by breakdown of starches from previous meals may contribute to growth of Streptococcus mutans. In any event, the saccharin compound will inhibit growth of the Streptococcus mutans regardless of whether it is employed with sugar.

The following in vitro tests were carried out in order to show that saccharin inhibits growth of Streptococcus mutans.

Seven strains of Streptococcus mutans (as shown in Table 1), representing the five Bratthall serological groups (Bratthall, 1970), were used in this study. Five of these strains are isolates from humans, and the other two strains are isoltaes from hamster and rat.

TABLE 1

Origin and Bratthall serological groups of the seven studied Streptococcus mutans strains.

| Strain number | Serological group | Origin |
|---|---|---|
| HS-6 | a | Hamster |
| AHT | a | Human |
| FA-1 | b | Rat |
| NCTC 10449 | c | Human |
| OMZ-176 | d | Human |
| B-2 | e/E | Human |
| P-4 | e/E | Human |

The Streptococcus mutans strains were maintained in a medium composed of 2% glucose (Bacto-Dextrose, Difco) and 2% yeast extract (Difco) at pH 6.5 in screw cap test tubes containing 9 ml, sterilized in an autoclave for 10 minutes at 20 lb./sq. in. and 126° C. The tubes were supplemented with 10% inoculum and were incubated at 28° or 36° C. The cultures were transferred every 4 to 5 days. The strains were preserved for a longer time period in Bacto Transport Medium Stuart (Difco) by inoculating 1 ml of a cell suspension to 5 ml of the transport medium in screw cap test tubes, mixing well, and freezing at −20° C. To reactivate these cultures, 1 ml of the thawed suspensions was added to 9 ml of yeast extract-glucose medium and incubated at 28° C. until growth appeared.

Stock solutions of sodium saccharin containing 2.8 g of sodium saccharin/20 ml of distilled water, were made up and sterilized by ultrafiltration. The solutions were then diluted to yield the desired saccharin concentrations. For each test, 1.0 ml of the appropriate saccharin dilutions and 0.5 ml of sterile water were added to 5.0 ml of a 2% glucose, 2% yeast extract medium at pH 6.5 in screw cap test tubes. The final concentrations of the saccharin in the medium were 2% (20 mg/ml), and 1/10, 1/20, 1/100 and 1/1000 of the 2% concentration.

The tubes were then inoculated with 0.5 ml of a 48 hour culture of each of the seven Streptococcus mutans strains to yield a total volume of 7.0 ml. Inoculated tubes with 1.5 ml of sterile water added to the glucoseyeast extract medium served as a control. The test tubes were incubated in a gyrotory water bath shaker (New Brunswick Scientific, Model G76) at 36° C. After 24 hours the optical density, as a measure of growth, was determined at 546 nm using a Bausch & Lomb Spectronic 20 Spectrophotometer, and the final pH was read using a Fischer Accumet Model 230 pH/ion meter.

All tests were carried out in duplicate and the obtained data were averaged to unify the experiment.

RESULTS

I. Growth and Fermentation Patterns of Streptococcus mutans in the Presence of Glucose To study the growth and fermentation patterns of Streptococcus mutans in the presence of glucose, the control data of all utilized strains were compared. Four distinct growth patterns could be observed:

Pattern 1: high rate of growth with low acid production (Strain OMZ-176)

Pattern 2: moderate growth rate with moderate acid production (Strains FA-1, AHT, HS-6)

Pattern 3: moderate growth rate with high acid production (Strains NCTC 10449, P-4)

Pattern 4: slow rate of growth with moderate acid production (Strain B-2)

Pattern 1 represents an extreme deviation from the expected pattern of growth. The atypically high pH of 4.65 and the high optical density of 0.99 suggest that the glucose is primarily incorporated into the cell for growth, while a relatively smaller amount of the glucose is converted to acidic end products, accounting for the higher pH value.

Pattern 2 agrees with the normally expected growth and fermentation. While all three strains yield moderate pH values in the 4.33 to 4.38 range, the differences in the optical density, ranging from 0.74 to 0.92, can be accounted for by the differences in their rate of growth. Strain FA-1 possesses the highest rate of growth of the three strains in this group. This suggests that more glucose is being utilized for accumulation of cell material as compared to the strains AHT and HS-6.

Pattern 3 deviates from the expected norm in that the pH of 4.15 and 4.19 is much lower than the norm. Since growth is moderate, O.D.=0.68 and 0.76, the low pH indicates that relatively more glucose is utilized for the acid yielding fermentation process as compared to glucose-C incorporated for cell growth.

Pattern 4 represents the other extreme in its pattern of growth. Strain B-2 is a slow grower, O.D.=0.55, and the produced pH of 4.44 is in the medium range. This observation may give indications as to the way glucose is utilized or may reflect a lower tolerance level of this strain to produced acids, thereby inhibiting its growth.

With the many strains of *Streptococcus mutans* that have been identified, this study demonstrates that there are several physiological patterns and differences within the species during glucose fermentation. No conclusions can be drawn with respect to trends within the five Bratthall serological groups, because of the limited number of strains tested.

II. The Effects of Sodium Saccharin on the Growth of Glucose-grown *Streptococcus mutans*

Sodium saccharin exerts a growth inhibiting effect on glucose-grown *Streptococcus mutans* throughout the studied concentration range from 0.02 to 20 mg/ml as shown in the attached FIGURE. As seen from the results for each of the concentrations 0.02 mg/ml (column 2), 0.2 mg/ml (column 3), 1 mg/ml (column 4), 2 mg/ml (column 5), 20 mg/ml (column 6) and control (no additions-column 1) for each of the seven strains of bacteria tested, the magnitude of the growth inhibition is proportional to the saccharin concentrations and affects all seven strains of *Streptococcus mutans* tested.

The following Examples further illustrate the present invention without, however, limiting the same thereto. All temperatures are expressed in °F.

EXAMPLE 1

A cherry flavor saccharin-sugar containing chewing gum is prepared from the following ingredients:

| Ingredients | Parts by Weight |
| --- | --- |
| Gum Base | 20 |
| Sugar | 50 |
| Corn Syrup | 16 |
| Dextrose | 10 |
| Lecithin | 0.2 |
| Citric acid | 0.5 |
| Fumaric acid (passes through a U.S. 140 mesh screen) | 2 |
| Free saccharin acid (passes through a U.S. 140 mesh screen) | 0.2 |
| Artificial cherry flavor | 1 |
| Gum arabic coated cherry flavor | 1.5 |

The gum base is melted (temperature 270°) and placed in a standard dough mixer kettle equipped with sigma blades. The corn syrup and lecithin are added and mixed for 2 minutes at 200°. At the time the mix is folding well, powdered free saccharin and powdered fumaric acid are added to the base-syrup mix and the mixture is mixed for 1 minute at 200°. Thereafter, the sucrose, dextrose, flavor oil, citric acid, and coloring agents are added and blended with the above mixture for 5 minutes at 160°. The resulting gum is discharged from the kettle and formed into gum sticks employing conventional techniques.

The chewing gum product obtained is found to have a pleasant balanced sweet-sour taste for up to 30 minutes and is effective in inhibiting growth of *Streptococcus mutans* in the oral cavity.

EXAMPLE 2

A peppermint flavor saccharin-sugar containing chewing gum is prepared from the following ingredients:

| | Parts by Weight |
| --- | --- |
| Gum base | 20 |
| Corn Syrup, 44° Be' | 17 |
| Powdered free saccharin acid (pulverized to pass through a U.S. 140 mesh screen) | 0.2 |
| Powdered Sugar (sucrose) | 50 |
| Dextrose | 10 |
| Peppermint oil | 1 |
| Lecithin | 0.2 |

The gum base is melted (temperature 270°) and placed in a standard dough mixer kettle equipped with sigma blades. The corn syrup and lecithin are added and mixed for 2 minutes at 200°. At the time the mix is folding well, powdered free saccharin is added and the mixture is mixed another 3 minutes at 200°. Thereafter, the sucrose, dextrose and flavor oil are added during which time the mixture is mixed another 3 minutes at 200°. Thereafter, the sucrose, dextrose and flavor oil are added during which time the mixture is mixed for 5 minutes. The gum is then discharged from the kettle, cut into 25 lb. loaves and allowed to cool to 90°–120° F. It is then rolled to a thickness of 0.178 cm on a standard Gimpel machine and scored into strips 7.26 cm wide and 41.9 cm long, and cooled for 12–18 hours.

The chewing gum product obtained is found to have a pleasant sweet taste for up to 30 minutes and inhibits growth of *Streptococcus mutans* in the oral cavity.

EXAMPLE 3

A spearmint flavor saccharin-sugar containing chewing gum is prepared from the following ingredients:

| | Parts by Weight |
| --- | --- |
| Gum Base | 20 |
| Sugar (sucrose) | 52 |
| Corn Syrup 44 Be' | 17 |
| Dextrose | 10 |
| Lecithin | 0.2 |
| Free saccharin (powdered - passes through a 140 U.S. mesh screen | 0.2 |
| Spearmint oil | 0.6 |

The gum base is melted (temperature 270°) and placed in a standard dough mixer kettle equipped with sigma blades. The corn syrup and lecithin are added and mixed for 2 minutes at 200°. At the time the mix is folding well, powdered free saccharin and flavor oil are mixed for 1 minute at 200°. Thereafter, the sucrose, dextrose and coloring agents are added and blended with the above mixture for 5 minutes at 160°. The resulting gum is discharged from the kettle and formed into gum sticks as described in Example 1.

The chewing gum product obtained is found to have a pleasant sweet taste for up to 30 minutes and inhibits growth of *Streptococcus mutans* in the oral cavity.

EXAMPLE 4

A spearmint flavor saccharin-sugar containing chewing gum is prepared from the following ingredients:

|  | Parts by Weight |
|---|---|
| Gum base | 18.5 |
| Sodium saccharin | 0.2 |
| Chalk | 3.3 |
| Sugar | 49 |
| Corn syrup | 17 |
| Lecithin | 0.2 |
| Sorbitol | 10 |
| Spearmint flavor (oil) | 1 |
| Spearmint (Spray-dried) | 0.5 |

The gum base is melted at 140°–150° F. and chalk premixed with sodium saccharin (particle size-64 microns and less) is added and the mixture mixed in a standard dough mixer equipped with sigma blades. Sugar is added and mixed for 3 minutes at 200°. Thereafter, liquid flavor is added and mixed for 2 minutes, a premix of lecithin and corn syrup is added and mixed for 3 minutes, sorbitol is added and mixed for 1 minute and spray dried flavor is added and mixed for 1 minute. The resulting gum is discharged from the kettle and formed into gum sticks employing conventional techniques.

The chewing gum product obtained is found to have a pleasant balanced sweet taste for up to 30 minutes and is effective in inhibiting growth of *Streptococcus mutans* in the oral cavity.

What is claimed is:

1. A method of inhibiting the growth of *Streptococcus mutans*, which consists essentially of the step of contacting *Streptococcus mutans* with a saccharin compound selected from the group consisting of sodium saccharin, ammonium saccharin, calcium saccharin or the free acid form of saccharin in an amount sufficient to inhibit growth of *Streptococcus mutans*.

2. The method as defined in claim 1 wherein said saccharin compound is sodium saccharin.

* * * * *